(12) United States Patent
Glinski et al.

(10) Patent No.: US 9,334,257 B2
(45) Date of Patent: May 10, 2016

(54) METHODS OF PURIFYING AND IDENTIFYING THE PRESENCE OF AND LEVELS OF PROCYANIDIN OLIGOMERIC COMPOUNDS

(71) Applicant: The Hershey Company, Hershey, PA (US)

(72) Inventors: Jan Glinski, Danbury, CT (US); W. Jeffrey Hurst, Mt. Gretna, PA (US)

(73) Assignee: The Hershey Company, Hershey, PA (US)

(*) Notice: Subject to any disclaimer, the term of this patent is extended or adjusted under 35 U.S.C. 154(b) by 0 days.

(21) Appl. No.: 14/537,321

(22) Filed: Nov. 10, 2014

(65) Prior Publication Data

US 2015/0133681 A1 May 14, 2015

Related U.S. Application Data

(63) Continuation-in-part of application No. PCT/US2013/040560, filed on May 10, 2013.

(60) Provisional application No. 61/645,836, filed on May 11, 2012.

(51) Int. Cl.
| | |
|---|---|
| *C07D 311/62* | (2006.01) |
| *C07D 311/64* | (2006.01) |
| *C07H 17/06* | (2006.01) |

(52) U.S. Cl.
CPC .................... *C07D 311/62* (2013.01)

(58) Field of Classification Search
CPC ..... C07D 311/32; C07D 311/64; C07H 17/06
See application file for complete search history.

(56) References Cited

U.S. PATENT DOCUMENTS

| | | | | |
|---|---|---|---|---|
| 6,015,913 A | * | 1/2000 | Kealey et al. | 549/386 |
| 2004/0176441 A1 | | 9/2004 | Romanczyk, Jr. et al. | |
| 2011/0301232 A1 | | 12/2011 | Howard et al. | |
| 2012/0021080 A1 | | 1/2012 | Venkatramesh et al. | |
| 2012/0022228 A1 | | 1/2012 | Giraud et al. | |

OTHER PUBLICATIONS

Robbins, R., "Analysis of flavanols in foods: what methods are required to enable meaningful health recommendations?." Journal of cardiovascular pharmacology 47 (2006): S110-S118.*
Yanagida, A., "Separation of proanthocyanidins by degree of polymerization by means of size-exclusion chromatography and related techniques." Journal of biochemical and biophysical methods 56.1 (2003): 311-322.*
Marston, A.,"Developments in the application of counter-current chromatography to plant analysis." Journal of Chromatography A 1112.1 (2006): 181-194.*
Hammerstone, J.F., "Identification of procyanidins in cocoa (Theobroma cacao) and chocolate using high-performance liquid chromatography/mass spectrometry." Journal of Agricultural and Food Chemistry 47.2 (1999): 490-496.*
Hammerstone, J.F., "Procyanidin content and variation in some commonly consumed foods." The Journal of nutrition 130.8 (2000): 2086S-2092S.*
Porter, L.J., "Flavans and proanthocyanidins." The flavonoids. Springer US, 1988. 21-62.*
Köhler, N."Preparative isolation of procyanidins from grape seed extracts by high-speed counter-current chromatography." Journal of Chromatography A 1177.1 (2008): 114-125.*
Ito, Y.,"Golden rules and pitfalls in selecting optimum conditions for high-speed counter-current chromatography." Journal of Chromatography A 1065.2 (2005): 145-168.*
The International Preliminary Report on Patentability, mailed Jul. 30, 2015, in related International Patent Application No. PCT/US2013/040560, filed May 10, 2013.

* cited by examiner

*Primary Examiner* — Samantha Shterengarts
*Assistant Examiner* — Matt Mauro
(74) *Attorney, Agent, or Firm* — David J. Kulik; Williams Mullen P.C.

(57) ABSTRACT

The invention provides methods of purifying and quantifying procyanidin oligomers from cocoa-containing sources. The methods advantageously provide ways to isolate commercially useful quantities of a range of procyanidin oligomers.

9 Claims, 7 Drawing Sheets

| Cocoa Procyanidin Oligomers | Estimated Purity (%) |
|---|---|
| Dimer; DP = 2 | 96 |
| Trimer; DP = 3 | 88 |
| Tetramer; DP = 4 | 85 |
| Pentamer; DP = 5 | 70 |
| Hexamer; DP = 6 | 70 |
| Heptamer; DP = 7 | 70 |
| Octamer; DP = 8 | 65 |
| Nonamer; DP = 9 | 60 |
| Decamer; DP = 10 | 50 |

Fig. 4

| Degree of polymerization | Test tube range | Fraction range | Partition coefficient |
|---|---|---|---|
| 1 (catechin) | 22-24 | 1 | 1.06 |
| 1 (epicatechin) | 25-36 | 2-5 | 0.84 |
| 2 (procyanidin B5) | 25-30 | 2-3 | 0.94 |
| 2 (procyanidin B2) | 34-48 | 5-9 | 0.63 |
| 3 | 34-57 | 5-12 | 0.52 |
| 4 | 40-68 | 7-12 | 0.41 |
| 5 | 65-96 | 14-22 | 0.33 |
| 6 | 81-124 | 19-29 | 0.26 |
| 7 | 121-160 | 29-37 | 0.18 |
| 8 | 156-195 | 35-44 | 0.14 |
| 9 | 186-240 | 43-53 | 0.11 |
| 10 | 221-262 | 50-59 | 0.08 |
| 11, 12 | 254-262 | 57-59 | ND |

Fig. 5

METHODS OF PURIFYING AND IDENTIFYING THE PRESENCE OF AND LEVELS OF PROCYANIDIN OLIGOMERIC COMPOUNDS

REFERENCE TO RELATED APPLICATIONS

This application claims priority benefit of U.S. provisional application 61/645,836 filed May 11, 2012, and is a continuation-in-part of PCT/US2013/040560 filed May 10, 2013, the entire contents of these prior applications are hereby incorporated herein by reference.

FIELD OF THE INVENTION

The invention relates to chromatography methods useful in identifying, purifying, and quantifying multiple oligomeric flavanol compounds. More specifically, and in one aspect, the invention relates to the use of liquid-liquid partition chromatography with extracts and samples from *Theobroma cacao* beans. In another aspect, the invention relates to a more efficient or simultaneous purification of multiple procyanidins or flavanol oligomers from a sample.

RELEVANCE OF THE INVENTION AND DESCRIPTION OF RELATED ART

Flavan-3-ol derivatives, such as catechins and procyanidin polymers, are prevalent antioxidant compounds of *Theobroma cacao* seeds or beans or nibs. Numerous reports have discussed the potential benefits of these compounds on human health and wellbeing. However, due to at least the complexity of their source from plant material, methods of purification, identification and quantification of specific polymers and oligomers of these compounds have been difficult to achieve in reliable and efficient ways. Generally, for food products and for cocoa products in particular, functional assays such as ORAC have been used to refer to the level of these compounds present. Commercial standards for comparison of many cocoa-derived oligomers are not available and thus limit the ability to produce reliable quantitative methods for isolation.

Centrifugal partition chromatography (CPC) is a relatively new and unique method of liquid-liquid partition chromatography. CPC enables the separation of components with nearly identical partition ratios and can be performed without the aid of a solid support.

CPC can be categorized in several ways. First, CPC is a type of countercurrent chromatography, which is an automated liquid-liquid extraction process permitting hundreds of automatic successive extractions. CPC is also a type of liquid-liquid partition chromatography, a technique involving a liquid stationary phase and a liquid mobile phase. The solute equilibrates between the stationary and mobile liquids. Finally, CPC utilizes a centrifugal force from a spinning rotor to effectively pump solutes through a column region and separate compounds.

CPC is unique because no solid support is used for the stationary phase. Instead, the liquid stationary phase is retained in a chamber by a combination of centrifugal force, the geometry, and the density difference between two liquid phases. The CPC apparatus consists of a rotor that employs a particular mode of motion. The rotor contains one or more chambers in which channels are engraved. The less dense stationary phase remains in the column because of the centrifugal force created by the spinning rotor. Consequently, the mobile phase is able to pass through the stationary phase.

When a mixture of components is introduced into the mobile phase of the CPC chamber, it distributes according to the individual components' distribution coefficients. The centrifugal force applied promotes the retention of the stationary phase against a continuous flow of mobile phase. The mobile phase flow enables the two phases to interact sufficiently for partition to occur, resulting in chromatographic separation.

The degree of separation in centrifugal partition chromatography depends primarily on the partition coefficient of the solute between the two solvent phases. Other important parameters in the separation process include mass transfer coefficients, flow rate, rotational frequency, and the identity of the two phases. A variety of the two-phase systems are possible using the CPC column. Both organic and aqueous systems are feasible. In fact, using CPC chromatography, aqueous two-phase systems can be used for separation. And, importantly, CPC can be used to separate racemic mixtures into chirally pure compounds.

BRIEF SUMMARY OF THE INVENTION

The invention, in one aspect, satisfies a need for efficient and reliable isolation methods for catechin compounds and oligomers that has intriguing commercial advantages on several fronts. Initially, it provides the art with an avenue to isolate individual procyanidin compounds that is straightforward and cost-effective. This allows one to use these isolated compounds in clinical studies. In addition, the methods allow one to quantitate multiple procyanidin oligomers more efficiently, and within the same sample or experiment. Similarly, by providing a standardized protocol for treating cocoa-containing samples and using CPC methods for purification or analysis, the invention potentially allows commercial or standardized ways to record levels of specific procyanidin compounds or subsets of specific procyanidin compounds that may be present in food ingredients or food products. In addition, the invention allows for the isolation of specific chiral-active oligomers from those present in cocoa or plant sources, for example.

Procyanidins are very common constituents of plants and are believed to be the second most common class of natural phenolic substances found in nature, after lignans. Because they are well represented in the Western diet, such as in cocoa, apples, and many berries, there is a growing interest in determining their pharmacological properties and significance as dietary antioxidants. Responding to these demands, the present invention involves a novel and advantageous approach to the preparative fractionation of cocoa procyanidins according to their degree of polymerization (DP) by applying a liquid-liquid (no solid support) chromatography, such as with a method known as Fast Centrifugal Partition Chromatography (FCPC) with commercialized rotors (for example, Kromaton, Annonay, France). The liquid-liquid system avoids the common problems in purifying flavonoids and flavan-3-ols, as they are prone to adhere to solid supports. In addition, as it is known that the chirality of cocoa flan-3-ols and flavanols effects their bioavailability and that distinct chiral species have differing biological activity, the methods can be used to isolate specific chiral compounds and subsets of chiral compounds from plants and cocoa in particular. Current methods involving a chiral HPLC column can be used to separate enantiomeric forms, but the time per run is in excess of an hour with minimal ability to scale up the process for larger quantities. Thus, CPC and FCPC as described here offers not only the ability to separate various enantiomeric forms but the scalability to isolate sufficient amounts on a cost effective basis so that they can be used in clinical and consumer studies.

In an experiment optimized for the best separation of procyanidin DP families between 4 and 12, one can employ a solvent system consisting of ethyl acetate-ethanol-water (6:1:5) in an ascending mode, wherein the mobile phase is the upper phase in each of the columns. However, other ratios of these solvents, as well as other, similar solvents as discussed herein, can be selected and used and one such example is ethyl acetate:ethanol:water (8:1:2). The procyanidin oligomers (DP2 to DP14) eluted with the mobile phase in an order of increasing DP, which is associated with an increasing polarity. The separation of bands between DP5 and DP9 was particularly impressive and advantageous in a context of the best preparative approaches reported for these compounds to date. The fractionation can be monitored by a normal phase HPLC analysis on a polyvinyl alcohol (PVA) column as well as by a C18 Reverse Phase (RP) column. To confirm and supplement this data, spectroscopic mass analysis of selected fractions by MALDI-TOF can be used. The Reverse Phase HPLC analysis reveals that in each DP family, the dominant peaks represented the linear epicatechin (4β-8) oligomers. However, using the FCPC fractionation approach, higher procyanidin oligomers can be separated and in advantageous quantities, such as those quantities required for evaluation of clinical or biological properties.

Thus, in one aspect, the invention relates to a scalable method for the bulk isolation and purification of cocoa procyanidin oligomers of varying length including DP2 through DP14, or subsets within this range of DP levels, such as DP2 through DP12 or DP 4 to DP12, as well as any specific procyanidin oligomer that may be present in plant and cocoa samples, including distinct or specific chiral species of the oligomeric compounds present in a fraction containing multiple oligomeric forms of a certain DP length. The methods and compositions of the invention are not limited to the oligomeric range DP2 to DP14, but this range is preferred. Thus, species higher than DP14 can be isolated from the methods of the invention.

In one aspect of the liquid-liquid partition chromatography methods of the invention, the invention includes a method of purifying at least one procyanidin oligomer compound from a cocoa-containing sample by optionally first defatting a cocoa-containing sample. The defatting step can comprise an extraction with a solvent comprising one or more of an alcoholic solvent, an aqueous solvent, or both an alcoholic and aqueous solvent. In other examples, the defatting step can be required. The examples below refer to various solvents that can be used. Other defatting methods or extractions can be used, such as extraction with hexane or acetone and other organic solvent extractions, as well as supercritical fluid extraction methods available in the art.

A solvent system of a mobile phase lipophillic solvent, a bridging solvent of one or more alcohols, and a stationary phase aqueous solvent can be selected for the intended or expected composition of the sample. The stationary and mobile phases can be reversed from those just stated or from those stated anywhere in this specification. In one example, the cocoa-derived samples (or extract) containing procyanidins DP3 to DP12 (or DP4 to DP12) can employ water or an aqueous solvent as the stationary phase solvent and ethyl acetate as the mobile phase solvent. However, the stationary and mobile phases can also be reversed, so that the stationary phase is ethyl acetate. The cocoa-containing sample is mixed with the mobile and stationary phase solvents and then added to a reservoir in a rotor. The rotor is prepared with multiple interconnected mixing chambers within it, each mixing chamber filled with or containing the stationary phase aqueous solvent. The cocoa-containing sample in the reservoir of the rotor enters one end of the mixing chambers and when the rotor is run or centrifugal force applied, the force allows the cocoa-containing sample to flow through multiple mixing chambers with the mobile phase solvent. As the components of the sample flow through the solvent, the components separate and exit at another end of the mixing chamber. Purified samples can then be collected. This method economically and quickly purifies one procyanidin oligomer in the exemplary range from DP3 to DP12, for example, from the other oligomers of differing DP.

A bridging solvent can be used and selected from those with a polarity between the polarities of the two phases (stationary and mobile). The bridging solvent dissolves partially in one phase as well as partially in the other. Thus, it can be used to modify the properties of both phases. For example, if an alcohol is used as a bridging solvent, the hydrophobic ethyl acetate solvent becomes more polar because it contains some alcohol. Also, the aqueous phase with bridging solvent alcohol becomes more lipophillic and a different range of organic substances can then dissolve in it. Without a bridging solvent, the polarities of the two phases are typically very pronounced such that some components of the sample are almost exclusively found in one or the other phase. This is not an ideal situation for a purification or separation because the components which are in the hydrophobic phase do not partition into the aqueous phase and thus would not be retained during a CPC run.

Accordingly, a bridging solvent can be selected that is preferably one of, or a mixture of one or more of, ethanol, methanol, isopropanol, and butanol. In general, the bridging solvent can be a C1 to C4 alcohol. The pH constraints imposed by solid supports such as silica and others are not a consideration with CPC. Thus, centrifugal partition chromatographic or liquid-liquid separations may be performed at virtually any pH, and the bridging solvent can also be used with a pH adjusted solvent for this purpose. For example, low pH can be used to preserve procyanidin content during the procedures, such as below pH 6 or at or below pH 4. In particular, the solvents and solutions that contact the procyanidin oligomers can optionally or preferably be maintained between about pH 3 to about pH 6 with an organic acid, with acetic acid being a preferred organic acid. Maintaining this pH range can preserve the levels of procyanidins present during the isolation process.

Purification with the methods of the invention can be combined with one or more additional or supplemental conventional purification procedures, such as solid phase chromatography or HPLC. Also, the method can avoid the use of additional purification procedures, like HPLC. In addition, the methods of the invention can be used to determine the amount of a specific procyanidin oligomer that is present in a particular cocoa sample. Exemplary methods for determining amounts and concentrations include spectroscopy, comparison to standards, and mass spectrometry. Thus, the methods can be used as a quantitative analysis of the procyanidin content of a sample.

As stated, the preferred sample is a cocoa-derived sample, but other plant-based materials can be used, such as apple, grapeseed, grape, pine bark, berries, cinnamon, pomegranate, acai, and other plants known to contain procyanidins or condensed tannins, or samples with detectable or high levels of these or procyanidin compounds. Where the method employs a cocoa-containing or cocoa-derived sample, it can be selected from one or more of chocolate liquor, cocoa powder, cocoa kibble, a cocoa extract, low fat cocoa powder, defatted cocoa powder, and non fat cocoa solids, for example.

The invention also includes a substantially purified procyanidin oligomer and/or a substantially purified chiral oligomer or subsets of specific and/or chiral compounds. For example, a purified composition of one or more procyanidin oligomers DP3 to DP12 that was derived from a cocoa-containing sample can obtained by the methods described here. Also, the purified composition can substantially consist of a single procyanidin oligomer selected from DP4 to DP12, meaning the sample primarily contains only one oligomer or procyanidin when analyzed by HPLC.

In preferred examples, the biphasic solvent mixture is a mixture of ethyl acetate, ethanol, and water, and in most preferred examples these solvents are present at a ratio of 6:1:5 respectively. Multiple FCPC mixing chambers or columns can be used, and the polarity of the biphasic solvent mixture can increase from a first chamber used to the last used. Effectively, and as shown in the data of FIG. 2, the number of chambers used and the FCPC conditions selected are capable of resolving separate bands for at least each of DP5 through DP9 procyanidin oligomers, or each of DP3 to DP12, or each of DP4 to DP12, or each of DP 4 to DP10, for example.

BRIEF DESCRIPTION OF THE DRAWINGS

FIG. 4 is a table of the purity levels of RP-HPLC purified procyanidin from cocoa samples.

FIG. 5 is a table showing the exemplary range of fractions collected for each oligomeric DP form. These fractions can be analyzed by HPLC and/or mass spectrometry to determine the procyanidin compounds present.

In FIG. 6, the Na ion adduct of oligomers DP10 through DP12 are shown at peaks corresponding to 2906, 3195, and 3482. In FIG. 7, the Na ion adduct of oligomers DP4 through DP9 are shown at peaks of approximately 1175, 1464, 1751, 2042, 2330, 2616.

DESCRIPTION OF THE INVENTION AND EXEMPLARY METHODS

Cocoa procyanidins can be isolated and quantified from a variety of cocoa sources, foods, food ingredients, or from *Theobroma cacao* beans. In general, the cocoa-containing sample is defatted prior to use in the CPC methods. Many defatting procedures are known or can be adapted for use here, such as using acetone, hexane, alcohols, or ether solvents in extractions. The catechins and procyanidins are generally found in the aqueous layers.

For preparative experiments, cacao bean samples expected to have high levels of procyanidins can be used. The Mexican lavado beans, available and used for decades from sources in Southern Mexico, are one example of beans with high levels of procyanidins. The lavado beans can be crushed and defatted, both mechanically to remove the cocoa butter fat and via solvent extraction. Insoluble matter can be cleared by simple centrifugation. The extracted aqueous liquid can be evaporated under vacuum to remove the solvent and then dried. This is effectively a cocoa solids sample or cocoa powder sample.

In one example, lavado cacao beans are defatted with hexane and extracted with an acetone:water:acetic acid mixture. Acetone is evaporated under vacuum pressure. The remaining liquid is freeze dried.

A sample is mixed with water and prepared for FCPC with a KROMATON device and rotor. Columns are prepared with biphasic solvent mixture of ethyl acetate:ethanol:water at 6:1:5 ratio. The solvent used can be modified from this ratio by calculating the partition coefficients and comparing to that of the ethyl acetate:ethanol:water example. The FCPC is run in ascending mode for purifying procyanidins, so that the mobile phase is the upper phase in the resting columns.

As shown in the results, an efficient and clear separation of the DP2 through DP10 bands can be accomplished in this manner, and preparative scale runs can be performed by increasing the volume of the samples and column sizes. However, modifications of the solvents used in the examples are possible. For example, alcohols like butanol could be used where isolation of the larger oligomers is preferred, such as DP5 to DP12, or DP9 to DP12 or even higher DP oligomers beyond DP12. Longer FCPC run or spin times can be used to facilitate the isolation of higher oligomers. Methanol can also be used in CPC runs with the solvent systems discussed here, and methanol is preferred in isolating the lower molecular weight DP fractions, such as DP2 to DP5, for example.

Figure 1:
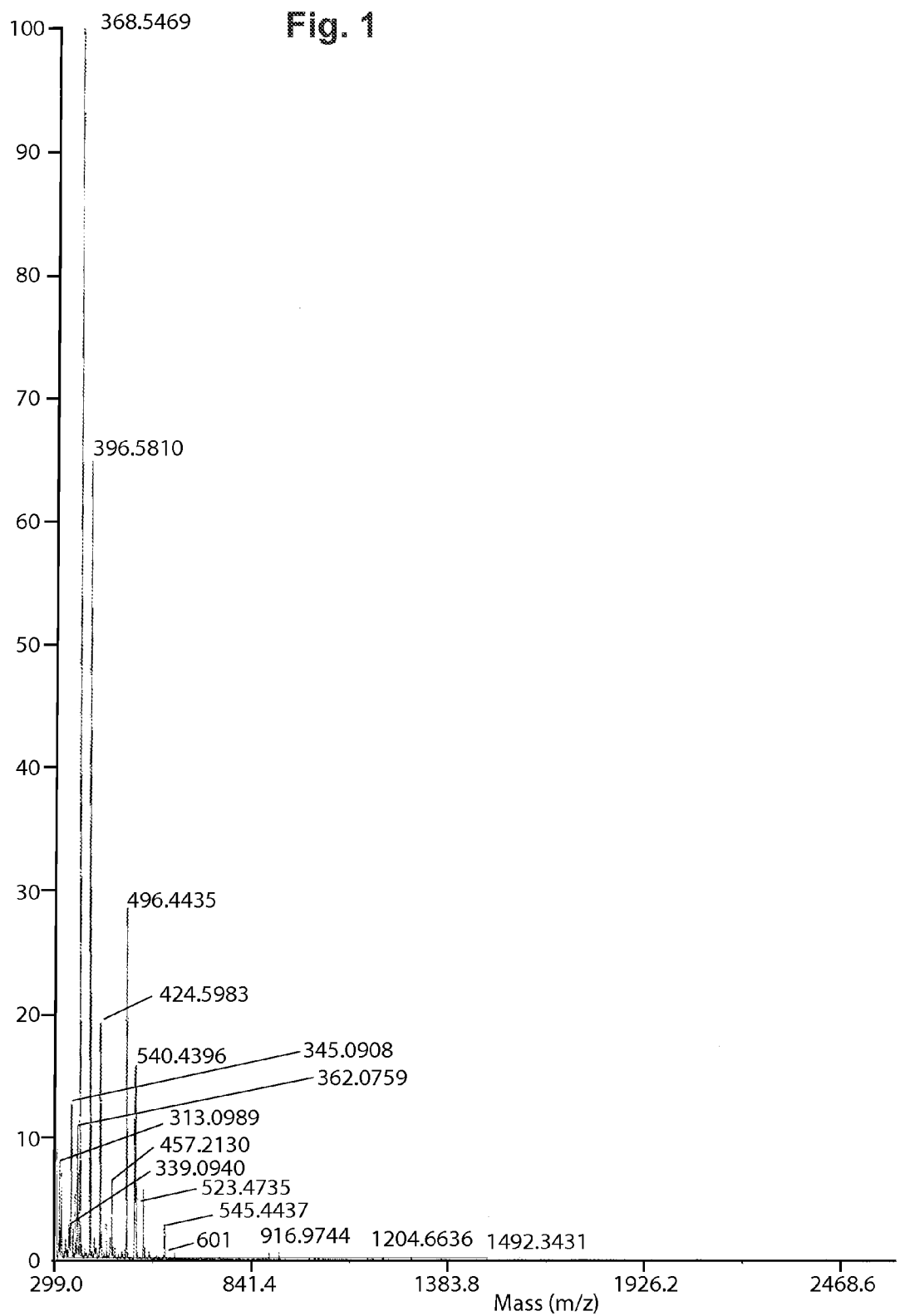
FIG. 1 depicts the MALDI-TOF analysis of CPC purified samples, showing peaks corresponding to the DP2 oligomer. The peak noted at "601" refers to the dimer coordinated with $Na^+$ ion.
Figure 6:
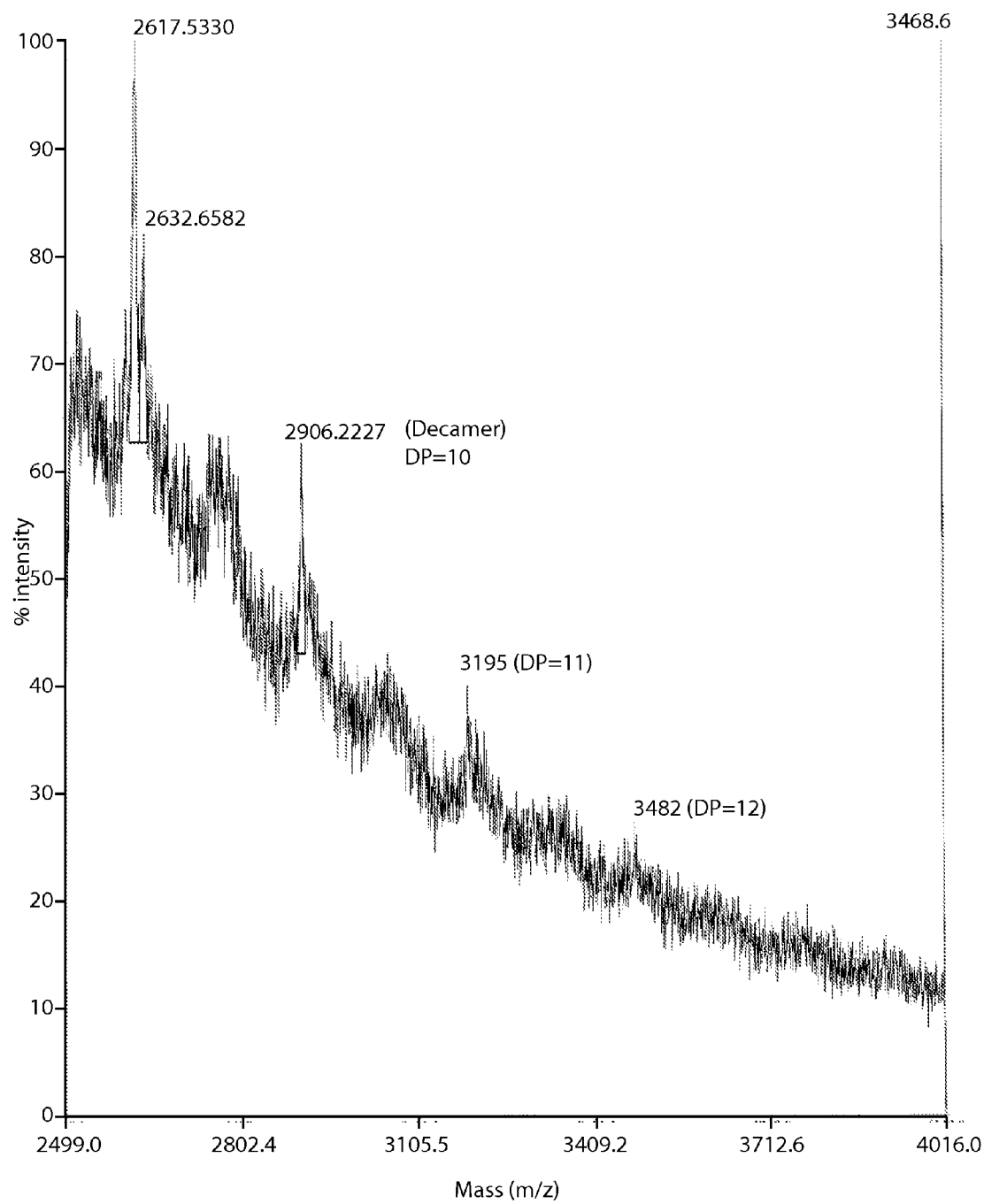
FIGS. 6 and 7 show mass spectra from MALDI-TOF analysis of an exemplary collection of purified fractions.
Figure 7:
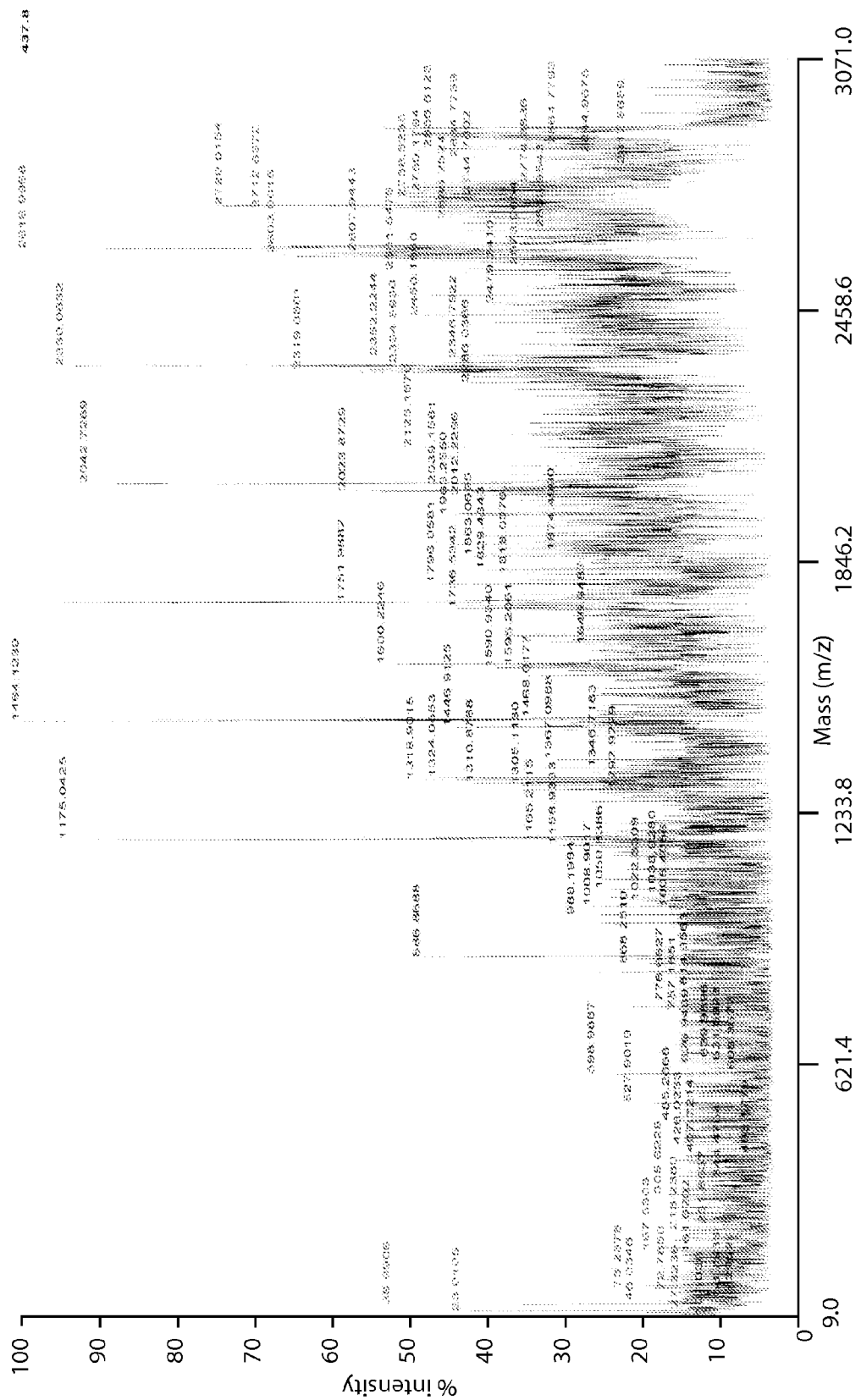

The isolated bands from FCPC can be assessed using MALDI-TOF mass spectrometry, for example. All bands from the FIG. 2 data can be confirmed as representing procyanidin oligomers DP2 through DP12. FIG. 1 shows the scan from the band corresponding to DP2, confirming its identity as DP2. Similarly, FIGS. 6 and 7 show the identification of each of DP4 through DP12.

Comparison with current methodology: To assess the chromatographic performance of FCPC compared to HPLC procedures, the purity results from Table 1 below can be compared to the HPLC purity shown in FIG. 4. Especially for the higher DP oligomers, the purity levels of FCPC samples surpass that of the HPLC.

TABLE 1

MALDI Data of Procyanidin Fractions

| Fraction | DP | Primary Mass from MALDI-TOF MS | % Purity |
|---|---|---|---|
| 141.6 | 2 | 601 | 85 |
| 141.9 | 3 | 889 | 80 |
| 141.13 | 4 | 1177 | 75 |
| 141.18 | 5 | 1465 | 75 |
| 141.24/25 | 6 | 1753 | 75 |
| 141.33 | 7 | 2041 | 70 |
| 141.41 | 8 | 2320 | 70 |
| 141.47/50 | 9 | 2617 | 70 |
| 141.53/56 | 10 | 2907 | 70 |

Figure 2:
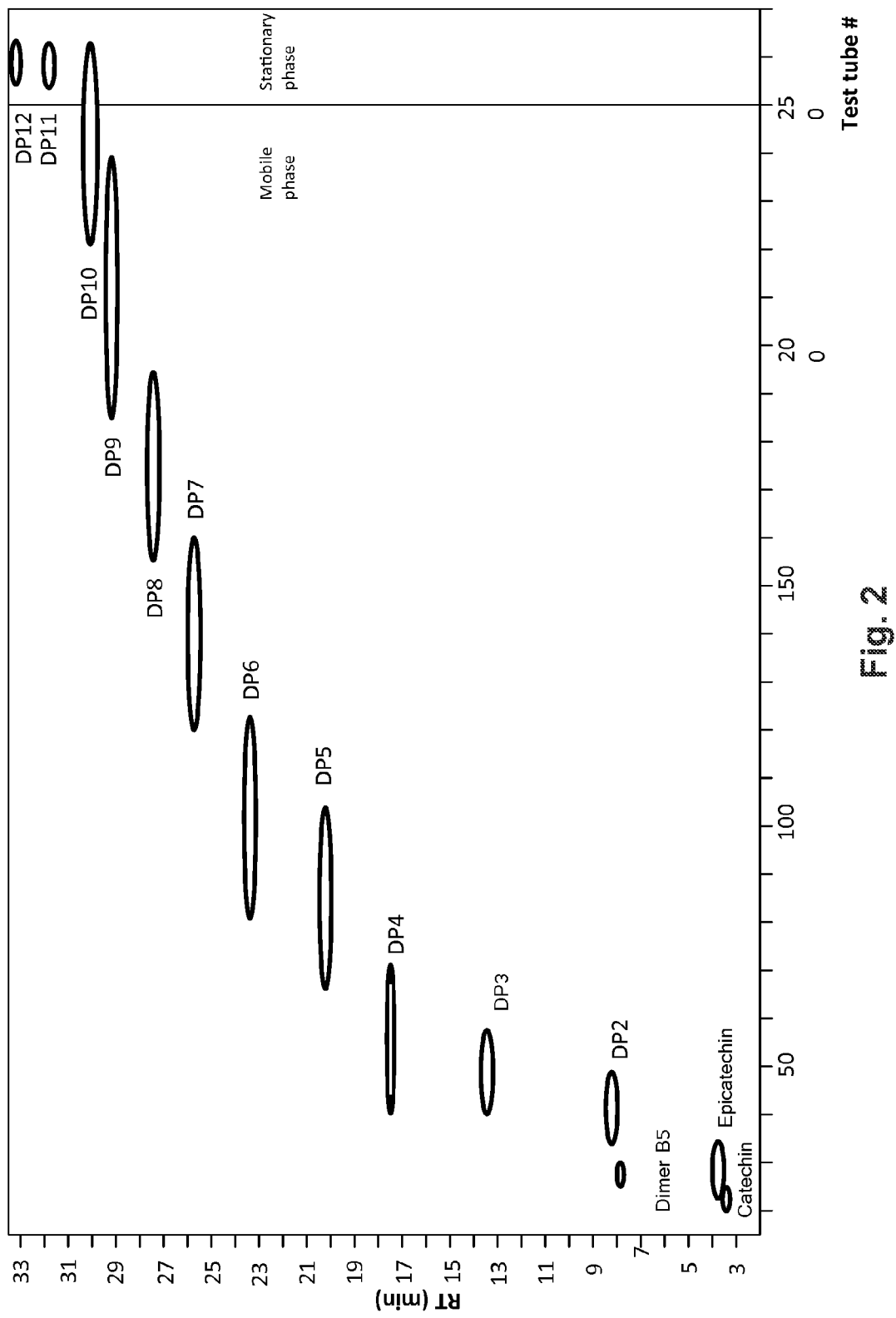
FIG. 2 depicts a chart representing the separation of DP2 through DP10 oligomers from a cocoa sample in an exemplary CPC method of the invention.
Figure 3:
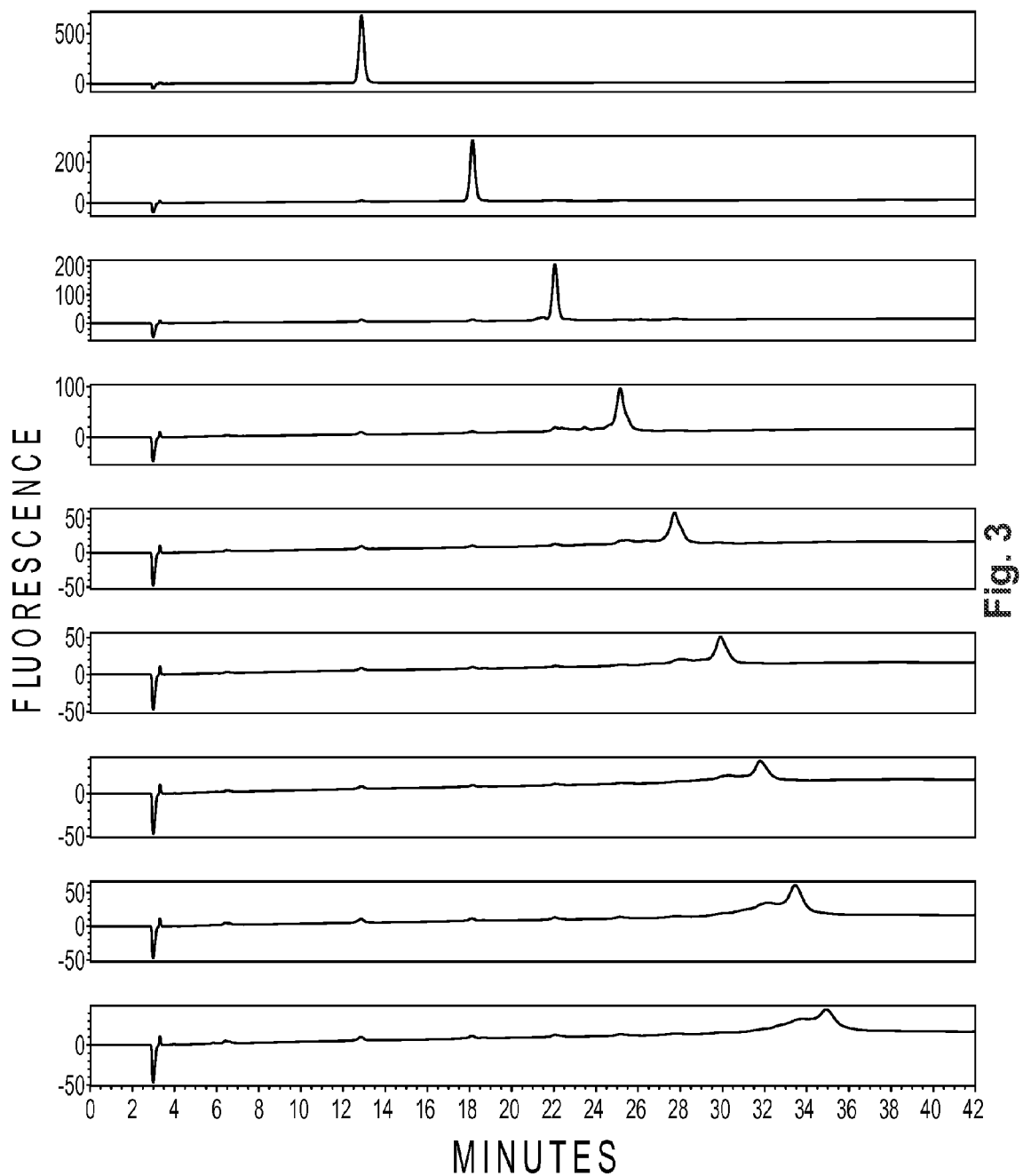
FIG. 3 depicts a RP-HPLC analysis of cocoa samples showing peaks of, from top to bottom, DP2 to DP 10.

The Table 1 data above refers to the peaks/fractions isolated in the FCPC results depicted in FIG. 2, where each of DP2 to DP12 were purified from one another from a defatted cocoa powder sample.

While a preferred solvent system is exemplified above, other solvents can be used. For example, a non-limiting set of solvent systems includes for the "mobile-stationary" phase as one of: ethyl acetate-water; methyl acetate-water; methylethyl ketone-water; and ethyl ether-water. Additionally, bridging solvents or modifying solvents can be selected from one or more of: methyl alcohol, ethyl alcohol, propyl or isopropyl alcohol, butyl or isobutyl alcohol, acetone, acetonitrile, hexane, methylene chloride, and chloroform. While many of these can be considered bridging solvents, some would not be, for example hexane and the chlorinated solvents may slow down the elution of the components in a sample.

Examples of solvents systems can also be selected from:
Ethyl acetate-methyl alcohol-water
Ethyl acetate-methyl alcohol-water
Ethyl acetate-ethyl alcohol-water
Ethyl acetate-methyl alcohol-ethyl alcohol-water (varying proportions)
Ethyl acetate-methyl alcohol-acetonitrile-ethyl alcohol-water (varying proportions)
hexane-ethyl acetate-ethyl alcohol-water
methyl ethyl ketone-butanol-water
methyl ethyl ketone-butanol-methanol-water The allowable volumes of the modifying solvents, or the respective volumes of each, are selected such that they do not homogenize both phases.

Table 2 below shows the results of the quantities of each DP (degree of polymerization) oligomer isolated from typical CPC runs as described herein. These quantities are isolated from an unfermented cocoa bean sample of 8.5 grams. In comparison, with a diol HPLC column, 150×30 mm, injecting about 270 mg of the same sample per run yields only about 25 mg of DP2-4 and less than 1 mg of DP11-12. Clearly, the CPC methods of the invention provide commercially viable methods for producing usable quantities of a range of procyanidin oligomers, especially from cocoa sources.

TABLE 2

| Degree of polymerization | Test tube range | Fraction range | Partition coefficient | Mass (mg) |
|---|---|---|---|---|
| 1 (catechin) | 22-24 | 1 | 1.06 | 154 |
| 1 (epicatechin) | 25-36 | 2-5 | 0.84 | 1751 |
| 2 (procyanidin B5) | 25-30 | 2-3 | 0.94 | skip |
| 2 (procyanidin B2) | 34-48 | 5-9 | 0.63 | 597 |
| 3 | 34-57 | 5-12 | 0.52 | 1132 |
| 4 | 40-68 | 7-12 | 0.41 | 588 |
| 5 | 65-96 | 14-22 | 0.33 | 858 |
| 6 | 81-124 | 19-29 | 0.26 | 939 |
| 7 | 121-160 | 29-37 | 0.18 | 372 |
| 8 | 156-195 | 35-44 | 0.14 | 284 |
| 9 | 186-240 | 43-53 | 0.11 | 134 |
| 10 | 221-262 | 50-59 | 0.08 | 255 |
| 11, 12 | 254-262 | 57-59 | ND | 135 |

Throughout this disclosure, applicants may refer to journal articles, patent documents, published references, web pages, and other sources of information. One skilled in the art can use the entire contents of any of the cited sources of information to make and use aspects of this invention, or any other information publicly available. Each and every cited source of information is specifically incorporated herein by reference in its entirety. Portions of these sources may be included in this document as allowed or required. However, the meaning of any term or phrase specifically defined or explained in this disclosure shall not be modified by the content of any of the sources. The description and examples that follow are merely exemplary of the scope of this invention and content of this disclosure and do not limit the scope of the invention. In fact, one skilled in the art can devise and construct numerous modifications to the examples listed below without departing from the scope of this invention.

What is claimed is:

1. A method of purifying at least one, individual procyanidin oligomer DP4 to DP12 from a cocoa-containing or cocoa-derived sample by liquid-liquid partition chromatography, the method comprising
defatting the cocoa sample;
selecting a solvent system of a mobile phase lipophillic solvent, a bridging solvent of one or more alcohols (C1 to C4), and water or aqueous solvent having a pH between about pH 6 and about pH 3, wherein the stationary phase can be selected as either the lipophilic solvent or water or aqueous solvent, and the mobile phase is selected as the other;
mixing the cocoa sample with the mobile and stationary phase solvents;
filling with stationary phase a rotor of a CPC apparatus having multiple interconnected mixing chambers within it, each mixing chamber containing the stationary phase solvent, and allowing the mixture of the cocoa-containing sample to be introduced into the rotor mixing chambers at one end;
spinning the rotor to allow the cocoa-containing sample to flow through multiple mixing chambers with the mobile phase solvent and to separate oligomers by degree of polymerization;
and collecting the at least one procyanidin oligomer DP4 to DP12.

2. The method of claim 1, wherein the stationary phase solvent is water.

3. The method of claim 2, wherein the mobile phase solvent is ethyl acetate.

4. The method of claim 3, wherein the bridging solvent is one of, or a mixture of more than one of, ethanol, methanol, isopropanol, acetone, and butanol.

5. The method of claim 1, wherein the collected procyanidin oligomer DP4 to DP12 is further purified by solid phase chromatography.

6. The method of claim 1, wherein the cocoa-containing sample is selected from one or more of chocolate liquor, unfermented cocoa beans, fermented cocoa beans, cocoa powder, cocoa extract, low fat cocoa powder, defatted cocoa powder, and non fat cocoa solids.

7. The method of claim 1, further comprising determining the amount of a procyanidin oligomer that is present in the cocoa-containing sample.

8. The method of claim 1, wherein the defatting step comprises extraction with a solvent comprising one or more of an alcoholic solvent, an aqueous solvent, or both an alcoholic and aqueous solvent.

9. The method of claim 1, wherein acetic acid is used to adjust the pH levels of the water or aqueous solvent.

* * * * *